(12) United States Patent
Fernandes et al.

(10) Patent No.: US 9,901,555 B2
(45) Date of Patent: Feb. 27, 2018

(54) TREATMENT OF VIRAL INFECTIONS

(71) Applicant: ENVIRON SKIN CARE (PTY) LTD, Kenilworth, Cape Town (ZA)

(72) Inventors: Brian Desmond Fernandes, Cape Town (ZA); Pamela Lee Ellwood, Cape Town (ZA)

(73) Assignee: ENVIRON SKIN CARE (PTY) LTD, Cape Town (ZA)

( * ) Notice: Subject to any disclaimer, the term of this patent is extended or adjusted under 35 U.S.C. 154(b) by 0 days.

(21) Appl. No.: 14/954,607

(22) Filed: Nov. 30, 2015

(65) Prior Publication Data

US 2016/0081953 A1    Mar. 24, 2016

Related U.S. Application Data

(62) Division of application No. 14/005,650, filed as application No. PCT/IB2012/051483 on Mar. 28, 2012, now Pat. No. 9,226,908.

(30) Foreign Application Priority Data

Apr. 4, 2011  (ZA) .................................. 2011/02483

(51) Int. Cl.
| | | |
|---|---|---|
| *A61K 31/19* | (2006.01) | |
| *A61K 9/00* | (2006.01) | |
| *A61K 47/10* | (2017.01) | |
| *A61K 47/14* | (2017.01) | |
| *A61K 47/36* | (2006.01) | |
| *A61K 9/06* | (2006.01) | |
| *A61K 47/12* | (2006.01) | |

(52) U.S. Cl.
CPC ............ *A61K 31/19* (2013.01); *A61K 9/0014* (2013.01); *A61K 9/06* (2013.01); *A61K 47/10* (2013.01); *A61K 47/14* (2013.01); *A61K 47/36* (2013.01); *A61K 47/12* (2013.01)

(58) Field of Classification Search
CPC ......... A61K 31/19; A61K 41/00; A61K 47/12
USPC .................................................. 514/557, 934
See application file for complete search history.

(56) References Cited

U.S. PATENT DOCUMENTS 5,827,884 A * 10/1998 Obagi ...................... A61K 8/25
                                                                424/63
2006/0263398 A1   11/2006 Kalil

FOREIGN PATENT DOCUMENTS

| WO | WO 97/09963 A1 | 3/1997 | |
|---|---|---|---|
| WO | WO 00/71105 A2 | 11/2000 | |
| WO | WO 03/079981 A2 | 10/2003 | |
| WO | WO 2008140673 A1 * | 11/2008 | ............ A61K 8/347 |
| WO | WO 2012/137106 | 10/2012 | |

OTHER PUBLICATIONS

Ali et al.; The efficacy of 5% trichloroacetic acid cream in the treatment of cutaneous leishmaniasis lesions (Abstract); Journal of Dermatological Treatment; Apr. 2012; 1 page; vol. 23, No. 2; Taylor & Francis.

Heithersay, et al.; "Tissue Responses in the Rat to Trichloracetic Acid—An Agent Used in the Treatment of Invasive Cervical Resorption"; Australian Dental Journal, Sydney, AU; vol. 33, No. 6, Jan. 1, 1988, pp. 451-461.

Osborne, et al.; "Herpes simplex and human papillomavirus genital infections: controversy over obstetric management."; PubMed; Clin Obstet Gynecol; Dec. 1990; vol. 33 (4) pp. 801-811.

* cited by examiner

*Primary Examiner* — Kevin E Weddington
(74) *Attorney, Agent, or Firm* — Thorpe North & Western, LLP

(57) ABSTRACT

The invention provides low concentration, stable compositions for the treatment of lesions associated with herpes viral infections. The compositions are in a form selected from creams and gels containing trichloroacetic acid in an amount of between 2.5% (m/m) and 6% (w/w) of the weight of the cream or gel.

13 Claims, No Drawings

TREATMENT OF VIRAL INFECTIONS

RELATED APPLICATIONS

This application is a divisional application of U.S. application Ser. No. 14/005,650, filed Sep. 17, 2013, which is a national stage entry under 35 U.S.C. 371 of International Application No. PCT/IB2012/051483, filed Mar. 28, 2012, which claims priority to South African Application No. 2011/02483, filed Apr. 4, 2011, which are each incorporated herein by reference.

DETAILED DESCRIPTION

THIS INVENTION relates to the treatment or control of viral infections. In particular, but not exclusively, the invention relates to the treatment of viral infections of the herpes type, including in particular herpes simplex I, herpes simplex II and herpes zoster.

Man himself is the reservoir of herpes virus hominis. It has been reported in one study that antibodies to herpes virus were found in 30-37% of college students, 62% of private patients and more than 80% of ward service patients. Although the virus is carried as a latent infection in a majority of individuals, in others an acute exacerbation of the activated virus takes place in a variety of forms and can be precipitated by a variety of factors, including traumatic factors such as sunlight, menstruation, and family upsets. Cold sores or fever blisters are believed to be caused by herpes simplex I, whereas herpes simplex II is thought to be the agent in genital herpes infections.

Herpes zoster (or simply zoster) causes the skin disease commonly known as shingles. This is a viral disease characterized by a painful skin rash with blisters in a limited area on one side of the body, often in the shape of a stripe. The initial infection with varicella zoster virus (VZV) causes the acute, short-lived, illness chickenpox and usually occurs in children and young people. Once an episode of chickenpox has resolved, the virus is not eliminated from the body but can go on to cause shingles which has very different symptoms, often many years after the initial infection.

Varicella zoster virus can become latent in nerve cell bodies and less frequently in non-neuronal satellite cells of dorsal root, cranial nerve or autonomic ganglion without causing any symptoms. In an immunocompromised individual, perhaps years or decades after a chickenpox infection, the virus may break out of nerve cell bodies and travel down nerve axons to cause viral infections of the skin in the region of the nerve. The virus may spread from one or more ganglia along nerves of an affected segment and infect the corresponding dermatome (an area of skin supplied by one spinal nerve) causing a painful rash. Although the rash usually heals within two to four weeks, some sufferers experience residual nerve pain for months or years. This condition is called postherpetic neuralgia. Exactly how the virus remains latent in the body and subsequently re-activates is not understood.

Throughout the world the incidence rate of herpes zoster every year ranges from 1.2 to 3.4 cases per 1,000 healthy individuals, increasing to 3.9-11.8 per year per 1,000 individuals among those older than 65 years. Antiviral drug treatment can reduce the severity and duration of herpes zoster, if a seven to ten day course of these drugs is started within 72 hours of the appearance of the characteristic rash. The amino acid lysine, which is a component of the proteins occurring in natural foodstuffs, is described in the literature as an anti-herpetic agent.

A striking feature of herpes infections is their occurrence in patients known to have an appreciable titer of herpes antibodies. The presence of antibodies is thus not a guarantee of protection against acute outbreaks. The route of infection of herpes virus appears to be by direct contact such as may occur between sexual partners, mother and child and even patient and dentist.

Oral herpes may take the form of recurrent labial lesions. Some patients have severe oral lesions causing considerable difficulty in eating. It has been estimated that up to a third of the population have recurrent episodes of oral infection and that over half of these patients have more than one attack each year. Viruses of the herpes group also cause severe disease in patients who are immunologically deficient, for example patients with HIV infections and particularly in patients being treated for cancer with drugs having immunosuppressive properties.

Ocular herpes and herpes encephalitis are additional forms of infections with herpes virus requiring continued and intensive medical attention not incorporating the treatment described. Genital herpes, which had an estimated incidence of 100,000 cases in the U.S. in 1973, had by 1980 been estimated to affect 30% of the sexually active population. The problem of herpes infections is thus a serious and growing one.

The present invention provides the use of trichloroacetic acid in the manufacture of a medicament for the treatment of viral infections by topical administration of a therapeutically affective amount of the medicament to a person or animal in need of treatment.

Prior art compositions of trichloroacetic acid have been in the form of liquids or thin gels which easily run after application. The Applicant is aware of WO 00/711 05 (A2) (Mezzoli) Trichloroacetic acid for the preparation of solutions and/or compositions for the treatment of erosive and/or ulcerative lesions, which is the closest prior art to the present invention known to the applicant. Mezzoli describes the use of aqueous solutions of trichloroacetic acid for the treatment of erosive and/or ulcerative lesions in which the concentrations of the trichloroacetic acid in the aqueous solution range from a minimum of 10% to a maximum of 90%, preferably from 10% to 50% and more preferably about 50%. Mezzoli indicates (see page 5 lines 12 and 13) that solutions of trichloroacetic acid with concentrations below 30% are unstable and have to be used within a very short time. Mezzoli also describes formulations of trichloroacetic acid in alcohol and ether and indicates that the higher the trichloroacetic acid concentration the more active the solution is, the shorter the period of treatment is and hence the lower the number of topical applications per day which is required. Mezzoli describes topical applications which vary from one to three times a day and reports that minor aphthous ulcerative lesions disappear within one to three days, and lesions heal in two to four days. In the case of ulcerative lesions from major aphtha, Mezzoli reports that pain and signs of inflammation disappear within three to five days and that the lesion heals within seven to eight days. Erosive or ulcerative lesions of the mucous membrane or of the cutis treated topically with the liquid trichloroacetic acid of Mezzoli in aqueous solution, or with pharmaceutical compositions comprising the same, become whitish due to the action of trichloroacetic acid on the lesion and on the mucosa and cutis around the lesion. The action of trichloroacetic acid and the whitish colour due to the action increase in intensity with increasing trichloroacetic acid concentration in the aqueous solution or the pharmaceutical composition.

The applicant has now found, surprisingly, that a formulation in the form of a cream or gel, which contains only 5% of trichloroacetic acid is very effective for the treatment of herpes lesions despite the commonly held belief amongst medical practitioners who deal with the treatment of such lesions that a concentration of 5% trichloroacetic acid in a pharmaceutical formulation would be ineffective. The results obtained with the formulation of the present invention are accordingly unexpected in the light of the widely held view that formulations containing low concentrations of trichloroacetic acid would be ineffective for the treatment of herpes lesions.

According to a first aspect of the invention, and there is provided a stable composition for the treatment of lesions associated with herpes viral infections, the composition being in a form selected from creams and gels and containing a low concentration of trichloroacetic acid, the amount of trichloroacetic acid being less than 6% (m/m) of the mass of the cream or gel.

The abbreviation "% (m/m)" refers to the percentage by mass of the trichloroacetic acid in a given mass of the composition. By a "low concentration" in the context of this specification is meant a trichloroacetic acid concentration which is less than 6% and, preferably, between about 2.5 and 5% (m/m). By a "stable composition" is meant a composition which is stable for at least 12-18 months. Prior art compositions containing less than 30% of trichloroacetic acid had been found to be substantially less stable, having shelf lives of less than about 6 months.

The amount of the trichloroacetic acid may be between about 1% and 5.5% (m/m), preferably between about 1.5% and 5% (m/m) and more preferably between about 2.5% and 5.0% (m/m). In a preferred embodiment of the invention the composition is in the form of a cream and the amount of trichloroacetic acid in the cream is about 5% (m/m). In another preferred embodiment of the invention the composition is in the form of a gel and the amount of trichloroacetic acid in the gel is about 2.5%.

An advantage of the composition of the invention is that the low concentration of the trichloroacetic acid will allow the composition to be marketed as an over-the-counter medication which can safely be applied by a purchaser and which will not require administration by a trained therapist. A second important advantage of the invention is that because the composition is in the form of a cream or gel it can easily and precisely be applied to a lesion. Prior art formulations such as that of Mezzoli are fluids or thin gels which cannot be precisely applied and which tend to run and therefore to come into contact with the skin around the lesion. Because these liquids or thin gels have concentrations of trichloroacetic acid which are much higher than the concentration of the composition of the invention, they affect the skin in the area around the lesion causing burning and peeling. The composition of the invention can be placed precisely on a lesion and will not run under the influence of the gravity so that it remains where applied for the duration of the treatment. Because it can be precisely applied and does not run the composition of the invention generally needs to be applied only once, following which the lesion dries and rapidly heals with minimal flaking within 24 to 48 hours. Prior art formulations such as the formulation of Mezzoli require one to three treatments per day over a period of two to four days and significant burning and peeling around the lesion takes place. The applicant is an expert in the field of the invention and is aware that the process of Mezzoli has not been successful and would be a painful and very inconvenient process. The Applicant is also of the view that the higher concentrations of trichloroacetic acid would prevent the formulations of Mezzoli from being sold as over-the-counter medications.

The composition may include pharmaceutically acceptable excipients, selected from viscosity builders, humectants (or wetting agents), emulsifiers, chelating agents and mixtures thereof. Emulsifiers are components which assist in keeping oil and water phases stable in an emulsion such as in a cream.

The viscosity builder may be selected from xanthan gum, hydroxypropyl guar, magnesium aluminium silicate, hydroxyethylcellulose and mixtures of any two or more thereof. The humectant may be selected from propylene glycol, butylene glycol, pentalene glycol, glycerine, sorbitol and mixtures of any two or more thereof. The emulsifiers may be selected from fatty alcohols, polyethylene glycol ethers of fatty alcohols, glycerol esters of long chain fatty acids, polyethylene glycol esters of long chain fatty acids and mixtures thereof. The chelating agent may be selected from ethylenediaminetetraacetic acid (EDTA), preferably as its sodium salt, tetrasodium glutamate diacetate, ethylenediamine-N,N'-disuccinic acid (EDDS) and mixtures of any two or more thereof.

The fatty alcohol may be a $C_{16}$-$C_{18}$ alcohol such as cetearyl (or cetostearyl) alcohol. The polyethylene glycol ether of the fatty alcohol may be ceteareth-20. The glycerol ester may be glyceryl stearate. The polyethylene glycol ester may be a polyethylene oxide stearate such as PEG-40 stearate.

In an embodiment of the invention, the composition may contain about 0.5% to 6.0% (m/m) of the trichloroacetic acid, about 5% to 15% (m/m) of the emulsifier, about 0.2% to 1.2% (m/m) of the xanthan gum, about 1% to 5% (m/m) of the propylene glycol and about 0.25% to 0.35% (m/m) of the EDTA as the sodium salt.

The composition may contain about 0.3% (m/m) of the EDTA.

In another embodiment of the invention, the composition may contain between 1.0% and 5% (m/m) of the trichloroacetic acid and may be used in a gel with slow-drying properties.

According to a second aspect of the invention there is provided a method of treating lesions associated with herpes viral infections, the method including topical administration of a stable composition selected from creams and gels and containing a low concentration of trichloroacetic acid, the amount of the trichloroacetic acid being less than 6% (m/m) of the weight of the cream or gel, in an amount sufficient to control the infection.

The composition may be as hereinbefore described.

The viral infection may be a herpes virus infection and may, in particular, be an infection caused by herpes simplex I, herpes simplex II or herpes zoster.

The Applicant has found that the medicament and method of the invention are effective in the treatment of lesions of the lips, mouth, gums, genitalia, trunk and limbs when applied in the form of a cream. The Applicant is aware that herpes infections can be aborted in the early stages by lowering the skin pH to a pH value of about 2. The Applicant is also aware that trichloroacetic acid at lower concentrations is well tolerated by the body tissues and surrounding tissues are not damaged by a short exposure to trichloroacetic acid. Paradoxically, higher concentrations of trichloroacetic acid are known to exacerbate herpes infections. The Applicant has now found that all herpes lesions are treatable and can be aborted by application of a trichloroacetic acid composition such as a cream containing between 1% and 5% of trichloroacetic acid or a gel containing about 2.5% of trichloroacetic acid.

For topical application, the trichloroacetic acid is preferably dispersed in the form of a fine powder in a conventional cream base at a concentration of between about 0.5% and about 5% (m/m), preferably about 5%. The cream is applied liberally to the affected parts and rubbed gently into the tissues. Applications may be made once or, for severe infections, every 12 hours for one to two days. The cream form may also be used for topical applications intrabuccally and intravaginally. The Applicant is aware that the herpes virus must first attach to a receptor on the cell surface before it can penetrate. This requires an intra-cellular alkalinisation and if there is a pH change to acidosis then the virus cannot attach and replicate. This prevents spread of the infection. The Applicant believes that the low dose trichloroacetic acid of the invention works in this way and provides an efficient, convenient and cost-effective treatment of a herpes virus infection. The change in skin pH caused by the topical application of the acid is in effect responsible for the therapeutic effects.

The advantages of the invention can be summarised as follows. The formulation of the invention is firstly not a solution, but a cream which can be easily and safely used by the end-consumer whereas prior art compositions are liquids which can be used only by trained clinicians. The cream of the invention does not cause pain and at the most causes a slight stinging sensation whilst prior art formulation sting or burn strongly and can be extremely uncomfortable. The cream of the invention is also stable and does not run whereas prior art products in the form of solutions or gels easily run down the surface of the skin under gravity and affect the skin adjacent to the lesion being treated.

The cream of the invention can also easily be packaged in small containers such as tubes which allow for easy dispensing of small quantities of the cream whereas prior art formulations are generally packaged in bottles from which the solutions are not easily dispensed. The cream of the invention is also not hazardous if it is spilled, whereas prior art formulations are potentially erosive acidic liquids. The skin surrounding the lesion can come into contact with the cream of the invention but because of the low concentration of trichloroacetic acid in the cream the surrounding skin is not affected whereas prior art formulations damage the surrounding skin, cause death of cells and a potentially deep peel. Because the surrounding skin is protected by its normal superficial barrier properties of the stratum corneum (horny layer) that are not destroyed by the low concentration of the trichloroacetic acid, the cells of the basal keratinocyte (growing) layer of the epidermis (upper layer of skin) are not damaged and so the healing process is accelerated. Higher concentrations of trichloroacetic acid as found in prior art formulations destroy the barrier of the epidermis and allow damage to the deeper layer of growing cells and retard healing.

The cream of the invention is stable for at least one year and so lends itself to over the counter sale whereas prior art formulations such as the formulation described in Mezzoli are unstable if the concentration of the trichloroacetic acid is less than 30%. In addition, the time of action is about four to five minutes for the cream whereas for the high concentration prior art formulations the exposure time is measured in seconds.

Even if the cream of the invention is misused, for example it is left on the skin for as long as ten minutes, the Applicant has found that they are still no ill effects. If prior art formulations such as that of Mezzoli are used to "double" expose the skin quite severe complications can arise and such exposure can result in severe scarring.

The cream of the invention generally requires application only once, following which the lesion dries up and it is generally not necessary for the cream to be used on successive days. Prior art formulations require one to three treatments per day until the wound is healed and this process takes from two to four days. In the healing process of the invention the lesion dries and may barely flake, whereas in the case of prior art formulations, peeling is a significant component of the healing phase. In addition, the cream of the invention does not require a specific type of applicator and can readily be applied by the finger tip, whereas the prior art formulation described by Mezzoli requires a specific type of applicator (see for example claims 12, 13 and 14 of Mezzoli).

The invention is now described by way of example with reference to the following Examples.

EXAMPLE 1

In different embodiments of the invention, gels or creams were prepared using trichloroacetic acid (1% to 5% m/m) the chelating agents disodium EDTA or tetrasodium glutamate diacetate (0.05 to 2% m/m), the emulsifier glyceryl stearate (0.5 to 10% m/m) or the emulsifiers cetearyl alcohol, glyceryl stearate, PEG-40 stearate and ceteareth-20 (1 to 10% m/m), the viscosity builder xanthan gum (0.1 to 1% m/m), the humectants propylene glycol (0.5 to 5% m/m) and water (to 100%). Tetrasodium glutamate diacetate is commercially available.

For the manufacture for the cream, the components were weighed on a calibrated digital scale. Depending on the batch size, a Mettler Toledo PB 3002-5 was used for smaller batches with individual components weighing up to 3 kg and for larger batches a larger Mettler balance was used. The various components were mixed in stainless steel vessels or plastic buckets.

The xanthan gum and the propylene glycol were first mixed to form a paste and the paste was added to a portion of the water and mixed thoroughly with a Silverson homogenizer to hydrate the xanthan gum. Glyceryl stearate and PEG-100 stearate and cetearyl alcohol, glyceryl stearate, PEG-40 stearate and ceteareth-20 were weighed and heated on a hot plate to 80° C. in a copper bottomed stainless steel container. A digital thermometer was used to measure the temperature.

The chelating agent, disodium EDTA and the emulsifiers glyceryl stearate, cetearyl alcohol, glyceryl stearate, PEG-40 stearate and ceteareth-20 were then added to the bulk of the water at 80° C., and homogenised with a Silverson Homogenizer at a high speed (typically 50,000 to 60,000 rpm) for 2-5 minutes according to batch size to produce an emulsion. The gum was added to the emulsion and the mixture was homogenised at a medium speed (typically about 25,000 rpm) to produce a homogenous material.

The material was allowed to cool naturally to <50° C. The active ingredient trichloroacetic acid, dissolved in an equal amount of cold water, was added while homogenizing at a medium speed (typically 25,000 rpm) till the bulk was shiny.

EXAMPLE 2

Treatment of Herpes I (Herpes Simplex) and Herpes II (Genital Herpes)

The affected skin area was cleaned and the cream containing 2.5% trichloroacetic acid prepared as described in Example 1, was applied in a small peasized amount (larger for more extensive lesions) to cover the infected area. The cream was applied in a sufficient quantity to produce a white opaque layer over the lesion. The cream was left on the skin for 4 minutes and then washed off with water. The lesions changed significantly by drying up and producing a light scab. If necessary, the lesions were treated again in the same way after a period of 24 hours.

EXAMPLE 3

Treatment of Herpes Zoster

The affected skin area was cleaned and the cream containing 2.5% trichloroacetic acid prepared as described in Example 1, was applied with a soft brush to cover the infected area. The cream was left on the skin for 4-10 minutes and then washed off with water. The lesions changed significantly by drying up. The lesions were treated again in the same way after a period of 24 hours. If there was a minimal change in the lesions and they remained uncomfortable, the cream was re-applied after 12 hours and then again after 24 hours. The treatments were repeated daily until it was clear that every lesion had settled. Generally a maximum of four days was required for herpes zoster.

What is claimed is:

1. A stable composition for the treatment of lesions associated with herpes viral infections, the composition being in a form of a cream or gel containing a low concentration of trichloroacetic acid, the amount of the trichloroacetic acid being in the range between 0.5% and 6% (m/m) of a mass of the cream or gel, the composition further including pharmaceutically acceptable excipients selected from the group consisting of viscosity builders, humectants, emulsifiers, chelating agents, and mixtures thereof.

2. The composition as claimed in claim 1, in which the amount of trichloroacetic acid is between 1.0% (m/m) and 5.5% (m/m).

3. The composition as claimed in claim 2, in which the amount of trichloroacetic acid is between 1.5% (m/m) and 5% (m/m).

4. The composition as claimed in claim 3, in which the amount of trichloroacetic acid is between 2.5% (m/m) and 5% (m/m).

5. The composition as claimed in claim 1, which is in the form of a cream.

6. The composition as claimed in claim 1, which is in the form of a gel.

7. The composition as claimed in claim 1, in which the viscosity builder is selected from the group consisting of xanthan gum, hydroxypropyl guar, magnesium aluminium silicate, hydroxyethylcellulose and mixtures of any two or more thereof.

8. The composition as claimed in claim 1, in which the humectant is selected from the group consisting of propylene glycol, butylene glycol, pentalene glycol, glycerine, sorbitol, and mixtures of any two or more thereof.

9. The composition as claimed in claim 1, in which the emulsifiers are selected from the group consisting of fatty alcohols, polyethylene glycol ethers of fatty alcohols, glycerol esters of long chain fatty acids, polyethylene glycol esters of long chain fatty acids, and mixtures of any two or more thereof.

10. The composition as claimed in claim 9, in which the fatty alcohol is cetearyl alcohol, the polyethylene glycol ether of the fatty alcohol is ceteareth-20, the glycerol ester of the long chain fatty acid is glyceryl stearate and the polyethylene glycol ester of the long chain fatty acid is PEG-40 stearate.

11. The composition as claimed in claim 1, in which the chelating agent is selected from ethylenediaminetetraacetic acid (EDTA), salts of ethylenediaminetetraacetic acid, tetrasodium glutamate diacetate, ethylenediamine-N,N'-disuccinic acid (EDDS), and mixtures of any two or more thereof.

12. The composition as claimed in claim 1, which contains between 0.5% and 6.0% (m/m) of the trichloroacetic acid, 5% to 15% (m/m) of the emulsifier, 0.2% to 1.2% (m/m) of xanthan gum, 1% to 5% (m/m) of propylene glycol and 0.25% to 0.35% (m/m) of ethylenediaminetetraacetic acid (EDTA) as a sodium salt.

13. A stable composition for the treatment of lesions associated with herpes viral infections, the composition being in a form of cream or gel containing a low concentration of trichloroacetic acid, the amount of the trichloroacetic acid being in a range between 0.5% and 6% (m/m) of a mass of the cream or gel, the composition further including pharmaceutically acceptable excipients comprising viscosity builders, humectants, emulsifiers and chelating agents, the viscosity builder including xanthan gum in a concentration of 0.2% to 1.2% (m/m), the humectant including propylene glycol in a concentration of 1% to 5% (m/m), the emulsifiers being selected from the group consisting of fatty alcohols, polyethylene glycol ethers of fatty alcohols, glycerol esters of long chain fatty acids, polyethylene glycol esters of long chain fatty acids and mixtures of any two or more thereof and being present in a concentration of 5% to 15% (m/m), and the chelating agent including ethylenediaminetetraacetic acid (EDTA) in a concentration of 0.25% to 0.35% (m/m).

* * * * *